United States Patent [19]

Moilliet et al.

[11] Patent Number: 5,162,584
[45] Date of Patent: Nov. 10, 1992

[54] FLUOROBENZENE DERIVATIVES

[75] Inventors: John S. Moilliet, Bury; Ian K. Jones, Burnage, both of England

[73] Assignee: Imperial Chemical Industries PLC, London, United Kingdom

[21] Appl. No.: 568,026

[22] Filed: Aug. 16, 1990

[30] Foreign Application Priority Data

Aug. 31, 1989 [GB] United Kingdom ............... 8919679

[51] Int. Cl.$^5$ ........................................ C07C 211/52
[52] U.S. Cl. .................................. 564/442; 558/419
[58] Field of Search ............... 564/442, 489; 558/419

[56] References Cited

PUBLICATIONS

Carey, F. A. *Organic Chemistry* pp. 748, 758–759 McGraw-Hill Book Co. (1987).
Tamelen, et al., Transition Metal Promoted Reductive Decyanation of Alkyl Nitriles JACS 93:7113 (1971).

*Primary Examiner*—Richard L. Raymond
*Assistant Examiner*—Brian M. Burn
*Attorney, Agent, or Firm*—Cushman, Darby & Cushman

[57] ABSTRACT

The invention relates to a process for the preparation of aminohalobenzenes which are useful as intermediates in the manufacture of agrochemicals, pharmaceuticals, and dyestuffs. The process involves the simultaneous hydrolysis in an acid medium of the two cyano groups in a 1,3-dicyanoaminohalobenzene to yield an aminohalobenzene.

2 Claims, No Drawings

FLUOROBENZENE DERIVATIVES

This invention relates to processes for the preparation of fluoroaromatics and to certain novel compounds.

It is an object of the present invention to provide a route to 2,3,5-trihaloanilines.

According to a first feature of the present invention there is provided a process for the preparation of a compound of the Formula (1):

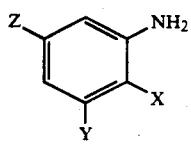

Formula (1)

which comprises hydrolysing a compound of Formula (2):

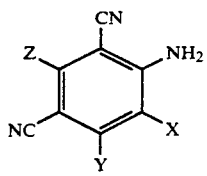

Formula (2)

wherein: X is —F or Cl; Y and Z are —F or —NH$_2$ provided that both Y and Z are not —NH$_2$;
in an acid medium.

According to another feature of the present invention there is provided a process for the preparation of a compound of Formula (3):

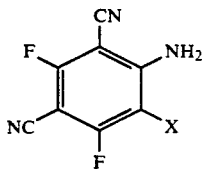

Formula (3)

which comprises reacting a compound of Formula (4):

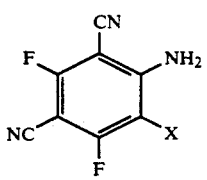

Formula (4)

wherein: X is —F or Cl;
with aqueous ammonia.

According to yet another feature of the present invention there is provided a process for the preparation of a compound of Formula (2) wherein X is —F or —Cl; and Y and Z are different and selected from —F and —NH$_2$; which comprises reacting a compound of Formula (4) with gaseous ammonia.

The compounds of Formula (1) wherein X, Y and Z are not identical are novel and form a further feature of the present invention. Specific examples of compounds of Formula (1) are those in which X is —F, Y is —F and Z is —NH$_2$; X is —Cl, Y is —F and Z is —NH$_2$; X is —Cl, Y is —NH$_2$ and Z is —F.

The compounds of Formula (2) are also novel and form a further feature of the present invention. Specific examples of compounds of Formula (2) are those in which X is —F, Y is —NH$_2$ and Z is —F; X is —F, Y is —F and Z is —NH$_2$; X is —Cl, Y is —NH$_2$ and Z is —F; X is —Cl, Y is —F and Z is —NH$_2$; X, Y and Z are all F; and X is Cl and Y and Z are F.

The hydrolysis of the compound of Formula (2) is preferably effected in an acid medium. The compound of Formula (2) is preferably added to a suitable acid solution at a temperature from 100° C. to 170° C., especially at 130° to 165° C. An example of a suitable acid solution is 77% sulphuric acid. The reaction is preferably continued until substantially complete which can take up to 7 hours.

In the preparation of the compound of Formula (3) by reaction of a compound of Formula (4) with aqueous ammonia, the compound of Formula (4) is preferably stirred in an inert liquid at a temperature from 40° C. to 80° C., more preferably 50° C. to 70° C. and especially 60° C. and ammonia solution is added to the reaction mixture until all the starting material is consumed.

In the preparation of the compound of Formula (2) by reaction of a compound of Formula (4) with gaseous ammonia, the compound of Formula (4) is preferably stirred in an inert liquid at a temperature from 40° C. to 80° C., more perferably 50° C. to 70° C. and the ammonia gas is passed through the reaction mixture until all the starting material is consumed. An example of a suitable solvent is 1,2-dimethoxyethane.

In the reaction of a compound of Formula (4) with gaseous ammonia it is preferred that in the compound of Formula (4) X is —F. In the derived compound of Formula (2) it is preferred that X is —F and that Y is —NH$_2$.

Where compounds of Formula (4) are reacted with gaseous ammonia any two of the —F groups may be replaced by —NH$_2$ and this produces mixed isomers. These isomers may be separated by appropriate means. Examples of appropriate means include fractional crystallisation of the hydrochloride salts of the aniline derivatives at a selected pH or acetylation followed by fractional distillation, optionally under vacuum.

Compounds of Formulae (1), (2), (3) and (4) are useful as intermediates in the preparation of agrochemicals, pharmaceuticals and dyestuffs.

The invention is further illustrated by the following examples in which all parts and percentages are by weight unless otherwise indicated.

EXAMPLE 1

20 parts of 2,4,5,6-tetrafluorobenzo-1,3-dinitrile was dissolved in 120 parts of 1,2-dimethoxyethane. 20 parts of aqueous ammonia solution (specific gravity=0.880) was added gradually over 1 hour. The reaction mixture was heated to 45° C. and stirred for 2 hours. The reaction mixture was cooled to 20° C. and drowned out into 150 parts of water. The resulting precipitate was filtered off, washed with water and dried under vacuum at 60° C. to give 13.3 parts (68%) of 6-amino-2,4,5-trifluorobenzo-1,3-dinitrile.

EXAMPLE 2

20 parts of 2,4,5,6-tetrafluorobenzo-1,3-dinitrile was dissolved in 100 parts of 1,2-dimethoxyethane at 20° C. Ammonia gas was bubbled through the solution for 25 minutes and the temperature was allowed to rise to 50° C. The reaction mixture was cooled to 20° C. and drowned out into 150 parts of water. The resulting precipitate was filtered off, washed with water and dried under vacuum at 60° C. to give 17.2 parts (89%) of 4,6-diamino-2,5-difluorobenzo-1,3-dinitrile.

EXAMPLE 3

10 parts of 4,6-diamino-2,5-difluorobenzo-1,3-dinitrile was added to 50 parts of sulphuric acid solution (77%) at 130° C. over 30 minutes. The reaction mixture was heated to 160° C. and this temperature was maintained for 4 hours. The reaction mixture was cooled to 20° C. and drowned out into 200 parts of water. The pH of the solution was adjusted to 2.5 with sodium hydroxide solution (48%) before extracting with 3×100 parts of ethyl acetate. The ethyl acetate was washed with water and removed by distillation to leave 58 parts (78%) of 1,3-diamino-2,5-difluorobenzene.

EXAMPLE 4

40 parts of 5-chloro-2,4,6-trifluorobenzo-1,3-dinitrile was dissolved in 150 parts of 1,2-dimethoxyethane. 30 parts of aqueous ammonia solution (specific gravity=0.880) was added gradually over 1 hour. The reaction mixture was heated to 60° C. and stirred for 30 minutes. The reaction mixture was drowned out into 300 parts of water. The resulting precipitate was filtered off, washed with water and dried under vacuum at 60° C. to give 33.6 parts (85%) of 6-amino-5-chloro-2,4-difluorobenzo-1,3-dinitrile.

EXAMPLE 5

21.7 parts of 5-chloro-2,4,6-trifluorobenzo-1,3-dinitrile was dissolved in 100 parts of 1,2-dimethoxyethane. Ammonia gas was bubbled through the solution for 10 minutes and the temperature was allowed to rise to 50° C. The reaction mixture was cooled to 20° C. and drowned out into 150 parts of water. The resulting precipitate was filtered off, washed with water and dried under vacuum at 60° C. to give 18.9 parts (88%) of a 3:1 mixture of 4,6-diamino-5-chloro-2-fluorobenzo-1,3-dinitrile and 2,4-diamino-5-chloro-6-fluorobenzo-1,3-dinitrile. These isomers may be separated by appropriate means.

EXAMPLE 6

5.1 parts of a 3:1 mixture of 4,6-diamino-5-chloro-2-fluorobenzo-1,3-dinitrile and 2,4-diamino-5-chloro-6-fluorobenzo-1,3-dinitrile was added to 28 parts of sulphuric acid (77%) at 130° C. over 20 minutes. The reaction mixture was heated to 160° C. and this temperature was maintained for 10 hours. The reaction mixture was cooled to 20° C. and drowned out into 200 parts of water. The pH of the solution was adjusted to 2.5 with sodium hydroxide solution (48%) before extracting with ethyl acetate. The ethyl acetate was washed with water and removed by distillation to leave 4.3 parts (87%) of a 3:1 mixture of 1,3-diamino-2-chloro-5-fluorobenzene and 1,5-diamino-2-chloro-3-fluorobenzene. These isomers may be separated by appropriate means.

We claim:

1. A process for the preparation of a compound of Formula (1):

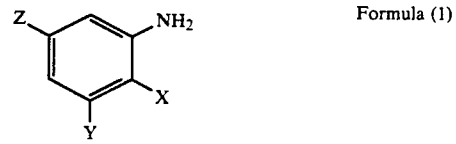

Formula (1)

which comprises hydrolysing a compound of Formula (2):

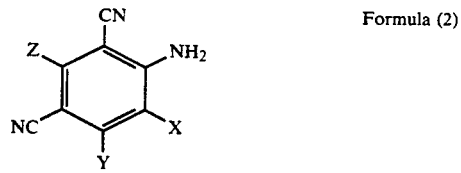

Formula (2)

wherein: X is —F or Cl; Y and Z are —F or —NH$_2$ provided that both Y and Z are not —NH$_2$; in an acid medium.

2. A process according to claim 1 wherein the hydrolysis is effected by treating the compound of Formula (1) with an acid at a temperature from 100° C. to 170° C.

* * * * *